United States Patent [19]

Prevedello et al.

[11] 4,331,568
[45] May 25, 1982

[54] 3,7-DIMETHYL-3-HYDROXY-6-OCTENENITRILE AND PROCESS FOR ITS PREPARATION

[75] Inventors: Aldo Prevedello; Edoardo Platone, both of San Donato, Italy

[73] Assignee: Snamprogetti S.p.A., Milan, Italy

[21] Appl. No.: 888,533

[22] Filed: Mar. 21, 1978

Related U.S. Application Data

[63] Continuation-in-part of Ser. No. 831,057, Sep. 6, 1977, which is a continuation-in-part of Ser. No. 627,350, Oct. 30, 1975, abandoned.

[30] Foreign Application Priority Data

Oct. 30, 1974 [IT] Italy .............................. 28955 A/74

[51] Int. Cl.$^3$ ................... A61K 7/46; C07C 121/34; C07C 120/00; C07C 121/30
[52] U.S. Cl. ........................... 252/522 R; 260/465.6; 260/465.9; 252/174.11
[58] Field of Search ............................. 627/350, 831; 260/465.6; 252/522

[56] References Cited

U.S. PATENT DOCUMENTS

| | | | |
|---|---|---|---|
| 3,354,196 | 11/1967 | Julia | 260/465.4 X |
| 3,755,411 | 8/1973 | Henrick et al. | 260/465.6 |
| 3,932,483 | 1/1976 | Schelling et al. | 260/465.6 |

OTHER PUBLICATIONS

Ivanov et al., C.A., 66, (1967), 37394v.
Vishnyakova et al., 70, C.A., (1969), 96901p.
Uchida et al., C.A., 72, (1970), 31371n.
Julia et al., C.A., 58, (1963), 10091b.
Rhone-Poulenc, C.A., 61, (1964), 9413h.
Weichet et al., C.A., 72, (1970), 132032h.
"The Chemistry of the Hydroxyl Group", edited by Patai, (1971), Interscience Pub. Co., pp. 689–690.
"Rodd's Chemistry of Carbon Compounds", 2nd ed., edited by Coffey, (1965), Elsevier Pub. Co., pp. 39–40.

*Primary Examiner*—Joseph Paul Brust
*Attorney, Agent, or Firm*—Morgan, Finnegan, Pine, Foley & Lee

[57] ABSTRACT

This invention relates to a new compound, 3,7-dimethyl-3-hydroxy-6-octenenitrile, useful for the preparation of compounds of the class of the octenenitriles. The method for the preparation thereof is furthermore disclosed, according to which 2-methyl-hept-2-ene-6-one is reacted with acetonitrile.

6 Claims, No Drawings

3,7-DIMETHYL-3-HYDROXY-6-OCTENENITRILE AND PROCESS FOR ITS PREPARATION

This application is a continuation-in-part of Ser. No. 831,057 filed Sept. 6, 1977 which is a continuation-in-part of Ser. No. 627,350 filed Oct. 30, 1975, now abandoned.

The present invention relates to a new compound i.e., 3,7-dimethyl-3-hydroxy-6-octenenitrile and to a process for its preparation.

The compound, object of the present invention, has the following structural formula:

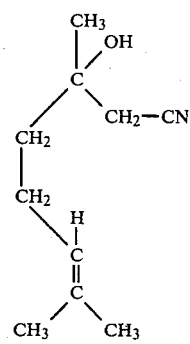

and is a suitable intermediate for organic synthesis. For example it is suitable material for the preparation of compounds belonging to the class of octenenitriles, as described in U.S. Pat. No. 4,028,395, compounds which, so far have been obtained by arduous and less selective chemical processes.

The compound 3,7-dimethyl-3-hydroxy-6-octenenitrile is a valuable perfume intermediate as it is less toxic than the prior art compound 2,6-dimethyl-2-hydroxy-heptenenitrile. In addition, the compound 3,7-dimethyl-3-hydroxy-6-octenenitrile is also a stabilizer for perfumes, when used in effective amounts for preventing deterioration of the scent of perfumes such as citral (geranialdehyde) which may be used as a scent for soap cakes or other compositions. Other perfumes or volatile oils which include fragrant aldehydes, terpenes, alcohols, ketones or phenols, which may be stabilized with the compound of this invention. These include volatile oils such as lemon, orange, bay, rose, lavendar and the like. Other volatile oils are well known and are exemplified by the materials listed in Remington's Practice of Pharmacy, 9th Edition, pp. 696-731 which is incorporated by reference.

3,7-dimethyl-3-hydroxy-6-octenenitrile is obtained by reacting 2-methyl-hept-2-ene-6-one with acetonitrile in the presence of strong bases and, particularly, of sodium amide in liquid ammonia.

The reaction temperature is kept among $-60°$ and $80°$ C. and the reaction product, after a fractional distillation in order to separate the final product from unreacted 2-methyl-hept-2-ene-6-one, has been identified by the data obtained by NMR, IR and mass spectroscopy. The new compound is obtained with good yields and selectivities, by the process described hereinafter.

The following examples, illustrative but not limitative of the present invention, disclose the process for obtaining such new compound.

EXAMPLE 1

Process for obtaining 3,7-dimethyl-3-hydroxy-6-octenenitrile

In a 5 flask, provided with a mechanical stirrer having glass blades, with a thermometer and a dropping funnel, were introduced 1500 cc of liquid ammonia from which water had been removed through a first passage on potassium hyroxide pellets and then through two passages on metallic sodium. The reaction temperature was kept at $-33°$ C.

0.9 g of finely subdivided ferric nitrate and then 1.5 g of metallic sodium were charged under stirring. The colour of the suspension had to change from blue to dark grey. Then more sodium (4.85 g) was charged during 10 minutes; after 15 minutes from the end of sodium addition, 10.25 g (0/25 mole) of anhydrous acetonitrile dissolved in 250 cc of anhydrous ethyl ether were added in 5 minutes.

After about 30 minutes, to the reaction mixture 31.5 g (0.25 mole) of 2 methyl-hept-2-ene-6-one dissolved in 250 cc. of anhydrous ethyl ether were added in 5 minutes. After 5 minutes the reaction mixture was quickly poured into a suspension of 100 g of ammonium chloride in 1000 cc of liquid ammonia. Ammonia was allowed to evaporate and the residue hydrolized with 500 cc of 3 N HCl. The two layers were separated; the aqueous layer was extracted three times with 200 cc of ethyl ether. The ether extracts were then combined and washed with 100 cc of a saturated bicarbonate solution and then with deionized water to neutrality. The organic phase was dried overnight on anhydrous sodium sulphate and then the solvent was removed by distillation. The residue was fractionated for separating 3,7-dimethyl-3-hydroxy-6 octenenitrile from unreacted 2-methyl-hept-2-ene-6-one. The hydroxynitrile, thus obtained, distilled at 98° C. at a pressure of 0.6 mmHg. The yield was 70%, while the selectivity was 90%, with a conversion of 88%.

The main characteristics of the new compound as obtained from NMR, IR and mass spectroscopy were the following:

| NMR (solvent CCl$_4$, internal standard HMDS) | |
|---|---|
| Proton type | chemical shift (ppm) |
| CH$_3$\C=CH—/CH$_3$ | 5.1 (t) |
| —OH | |
| —OH | 3.3 (s) |
| —CH$_2$—CN | 2.5 (s) |
| —CH$_2$—CH=C(CH$_3$)(CH$_3$) | 1.9 (m) |
| —CH=C(CH$_3$)$_2$ | 1.6 (d) |
| —CH$_2$—C(OH)(CH$_3$)— | 1.45 (m) |
| —C(OH)(CH$_3$)—CH$_2$—CN | 1.3 (s) |

The infrared spectra confirms the presence of the following functional groups:
IR: —OH stretching 3460 cm$^{-1}$
—CN stretching 2260 cm$^{-1}$
The molecular weight by mass spectroscopy is 167.

EXAMPLE 2

In a 5 l flask, provided with a mechanical stirrer having glass blades, with a thermometer and a dropping funnel were introduced 1500 cc of liquid ammonia from which water has been removed through a first passage on potassium hydroxide pellets and then through two passages on metallic sodium.

The reaction temperature was kept at −33° C. 1 g of anhydrous ferric chloride and then g 8 of metallic sodium were charged under stirring.

After about 15 minutes other sodium (42.8 g; in all 50.8 g equal to 2.2 moles) was charged in 10 minutes; after 15 minutes, from the end of sodium addition were charged 82 g (2 moles) of anhydrous acetonitrile diluted with about 250 cc of anhydrous ethyl ether.

After about 30 minutes 252 g (2 moles) of 2 methyl-hept-2-ene-6-one diluted with 250 cc of anhydrous ethyl ether were charged in the reaction mixture during 5 minutes.

After 5 minutes the reaction mixture was poured in a suspension of 400 g of ammonium chloride in 100° cc of anhydrous ammonia. The ammonia was allowed to evaporate and the solid residue was hydrolyzed by the addition of 3 N hydrochloric acid to neutrality. The two layers were separated and the water layer was extracted with ethyl ether. The ether extracts were combined and dried overnight on anhydrous sodium sulphate. After the solvent was removed, the residue was fractionated under vacuum for separating 3,7-dimethyl-3-hydroxy-6-octenenitrile from unreacted 2 methyl-hept-2-ene-one.

The selectivity and conversion (calculated by gas chromatography in residual crude product) were respectively 91% and 87%.

EXAMPLE 3

Use of 3,7-dimethyl-3-hydroxy-6-octenenitrile as a perfume stabilizer 20 grams of citral (commercial, by FLUKA) were divided into two equal portions. To one portion, 5% of 3,7-dimethyl-3-hydroxy-6-octenenitrile (i.e. 0.5 gram) was added. These two samples (A is the sample as such, B the sample with the 5% of the 3,7-dimethyl-3-hydroxy-6-octenenitrile) were used (1 gram) for perfuming soap cakes whereas the remainder was maintained in two beakers left in the ambient air in a closed environment.

Test with scented soap cakes.

Two soap cakes were prepared by mixing 100 grams of laundry (Marseilles) soap comminuted with 1 gram of sample A and 100 grams of the same soap with 1 gram of the sample B. With these two mixtures there were prepared two soap cakes from each admixture, with prolonged extrusion of homogeneization purposes and then cake pressing.

The scent of the soap cakes, as prepared, were identical. The cakes were then maintained in the air and light in a closed room for 30 days and tested twice in a week to ascertain the scent variations, if any. The two cakes with the sample A, since the second check, showed a definite diminution of the scent and the scent was virtually absent after the second week. Conversely, the cakes containing the sample B after 1 month had the same scent and perfume intensity as at the start of the test.

Test on liquid samples.

At the same expiry times as in the previous tests on soap cakes, also the scent of the substance kept in the beakers were checked. For sample A a gradual weight drop was seen the very outset and this was considerably greater than that observed for the sample B. In the case of the sample A a gradual alternation of the odoriferous properties was observed, whereas the properties of sample B remained unaltered up to the completion of the test. The scent evaluations was carried out by four technicians, who were not aware of the nature of the samples and not even of the purpose of the tests.

What we claim is:

1. A composition which comprises a perfume and an amount of 3,7-dimethyl-3-hydroxy-6-octenenitrile which is sufficient to stabilize the scent of said perfume.

2. A composition as defined in claim 1 wherein the perfume is citral.

3. A composition as defined in claim 1 wherein 5% of 3,7-dimethyl-3-hydroxy-6-octenenitrile is employed.

4. A method for the prevention of the deterioration of the scent of a perfume said method comprising adding to the perfume an amount of 3,7-dimethyl-3-hydroxy-6-octenentrile which is sufficient to prevent deterioriation of the scent of said perfume.

5. A method as defined in claim 4 wherein the perfume is citral.

6. A method as defined in claim 5 wherein 5% of 3,7-dimethyl-3-hydroxy-6-octenenitrile is employed.

* * * * *